United States Patent
Neuenschwander

(10) Patent No.: US 8,562,671 B2
(45) Date of Patent: Oct. 22, 2013

(54) SCAFFOLDS FOR ARTIFICIAL HEART VALVES AND VASCULAR STRUCTURES

(75) Inventor: Peter Neuenschwander, Baden (CH)

(73) Assignee: Eidgenossische Technische Hochschule Zurich, Zurich (CH)

( * ) Notice: Subject to any disclaimer, the term of this patent is extended or adjusted under 35 U.S.C. 154(b) by 166 days.

(21) Appl. No.: 12/303,897

(22) PCT Filed: Jun. 4, 2007

(86) PCT No.: PCT/EP2007/004927
§ 371 (c)(1),
(2), (4) Date: Feb. 27, 2009

(87) PCT Pub. No.: WO2007/140964
PCT Pub. Date: Dec. 13, 2007

(65) Prior Publication Data
US 2010/0168832 A1    Jul. 1, 2010

(30) Foreign Application Priority Data

Jun. 9, 2006  (EP) ..................... 06011911

(51) Int. Cl.
*A61F 2/06* (2013.01)
*A61F 2/24* (2006.01)
*B29C 33/40* (2006.01)
*B29C 67/00* (2006.01)
*D04H 3/16* (2006.01)

(52) U.S. Cl.
USPC ........... 623/1.49; 623/2.1; 623/2.42; 623/1.1; 623/1.39; 623/1.41; 264/225; 442/401

(58) Field of Classification Search
USPC .......................... 264/2.25; 623/1.49; 442/401
See application file for complete search history.

(56) References Cited

U.S. PATENT DOCUMENTS

| | | | |
|---|---|---|---|
| 3,655,306 A | 4/1972 | Ross et al. | |
| 5,665,831 A * | 9/1997 | Neuenschwander et al. | 525/415 |
| 6,454,811 B1* | 9/2002 | Sherwood et al. | 623/23.76 |
| 6,955,775 B2* | 10/2005 | Chung et al. | 264/10 |
| 2004/0254640 A1 | 12/2004 | Sutherland et al. | |
| 2006/0085063 A1* | 4/2006 | Shastri et al. | 623/1.41 |
| 2006/0178477 A1 | 8/2006 | Neuenschwander | |
| 2006/0195142 A1* | 8/2006 | Shalaby | 606/228 |
| 2008/0131965 A1 | 6/2008 | Baaijens | |
| 2009/0318962 A1* | 12/2009 | Spedden et al. | 606/228 |
| 2010/0093093 A1* | 4/2010 | Leong et al. | 435/396 |

FOREIGN PATENT DOCUMENTS

| | | |
|---|---|---|
| EP | 0 696 605 A1 | 2/1996 |
| EP | 1 452 189 A | 9/2004 |
| EP | 1 452 190 A | 9/2004 |
| WO | WO 2005/007210 A1 | 1/2005 |
| WO | WO 2005/106090 A2 | 11/2005 |

* cited by examiner

*Primary Examiner* — Thomas J Sweet
*Assistant Examiner* — Jacqueline Woznicki
(74) *Attorney, Agent, or Firm* — Alston & Bird LLP

(57) ABSTRACT

The invention relates to scaffolds for artificial heart valves and vascular structures comprising a biocompatible block copolymer. A method and means for producing said scaffold are also provided.

19 Claims, 6 Drawing Sheets

SCAFFOLDS FOR ARTIFICIAL HEART VALVES AND VASCULAR STRUCTURES

CROSS-REFERENCE TO RELATED APPLICATIONS

This application claims the benefit of European Patent Application No. EP 06 011 911.2, filed Jun. 9, 2006, which is incorporated herein by reference in its entirety.

FIELD OF THE INVENTION

The present invention relates to scaffolds for artificial heart valves and vascular structures. A method for producing said scaffolds and means to use said method are also provided.

BACKGROUND OF THE INVENTION

Vascular and heart diseases are among the most prominent diseases in western world. In particular, heart diseases are the leading cause of death. In recent years, a possibility to treat such illness, that became increasingly popular and successful, employs transplantation of organs or structural parts, e.g. heart valves in the case of heart valve dysfunction. However, the potential recipients far outnumber the present donors of the organs needed. Thus the growing demand creates a constant need for artificial organs or structures that can at least temporarily replace the natural organs.

Currently, synthetic implants or natural implants of animal origin are used to overcome the gap between the number of available natural donors and potential recipients. Yet, they bear quite a number of disadvantages.

Synthetic implants may lead to complications such as thrombosis, a risk which is increased due to changes in the blood flow caused by artificial heart valves. That is why patients with artificial heart valves permanently need anticoagulant medicaments. In addition, such patients are prone to infections causing life-threatening complications.

Implants of natural origin used for replacement of heart valves are usually derived from porcine or cow. The porcine or cow tissue is treated with glutar-aldehyde. These biological implants have the disadvantage that they tend to degenerate after twelve to fifteen years. Thus, they are not suitable for younger patients. Another risk inherent to biological implants is the transmission of pathogens, in particular viruses. It is also possible, that biological implants trigger unwanted and often fatal immune reactions by the host immune system, since the material may be recognized as foreign tissue.

A further disadvantage of artificial implants such as heart valves lies in the fact that these structures are not living structures and therefore cannot undergo any repair or growth processes as needed by the host. Especially younger patients thus need multiple surgeries which itself increases the mortality risk.

Thus, there is a need for implants comprising artificial structures, e.g. a scaffold, that can be used to culture cells. By culturing cells on such a scaffold one tries to prepare hybrid structures which may serve as implants and provide specific functions. Such processes are also termed tissue engineering.

Tissue engineering includes the preparation of suitable scaffolds that are biocompatible and preferably degradable. Such hybrid implants should at least temporarily provide a biomechanical structure that allows the cultured cells to form the tissue or structure needed as far as this is possible.

Biocompatible materials employed in prior art for the above describes purposes are polyglycolic acid (PGA), polyhydrooctanoate (PHO) and polyhydroxyalcanoate (PHA). However, neither of these materials unites all the properties needed in terms of mechanical stability and biocompatibility. Implants comprising PGA are brittle. Implants comprising PHA lack the required rate of degradability and degrade only very slowly in a patient's body.

BRIEF SUMMARY OF THE INVENTION

The problem solved by the present invention is to provide biocompatible scaffolds that can be manufactured in the desired form and which provides excellent properties for cells grown on or inside it and which are suitable for use in implants.

The problem is solved by a scaffold according to claim 1. Further preferred embodiments are subject-matter of the dependent claims.

A scaffold of the present invention comprises an electrospun mesh of a block copolymer which is highly biocompatible and also biodegradable. The degradability can be precisely controlled by slightly changing the chemical composition of the biocompatible block copolymer.

The base material of the scaffold is a pure polymer. No further additives, e.g. stabilizers, antioxidants or plastifiers, which could adversely affect the excellent biocompatibility, are needed. Further advantageous properties are the elasticity while still maintaining excellent mechanical stiffness. The mechanical properties strongly depend on the properties of the crystalline and the non-crystalline domains of the bulk polymer.

Scaffolds according to the present invention have a mesh-like structure formed by polymer fibers. The mesh structure comprises open pores which are present throughout the entire scaffold and which are distributed in a random statistical way throughout the structured scaffold In addition, the average pore size varies only within a limited range. The porosity and the pore size of the scaffold of the present invention can be varied to some extent according to needs of the intended use making the scaffolds a very versatile tool. Porosity can on one hand be controlled by the concentration of the block copolymer solution and on the other hand by the choice of the solvent as by some processing parameters of the electrospinning process. All parameters which contribute to the stiffness of the fibres at the time point of their deposition on the target, give less dense mesh structures. Cooling of the target to low temperatures is therefore a tool to control the mesh density. The targets are cooled to a temperature in the range of −190° C. to 0° C., preferably in the range of −65° C. to −55° C., and most preferably to about −60° C. For instance, the target can be cooled by cooling means, e.g. by applying cold gases to the target. Preferred examples for such cold gases are evaporating liquid nitrogen or cold $CO_2$. In general, a section through a scaffold shows that the polymer layer forming the scaffold comprises about 10% fibres forming a mesh and about 90% open pores. This property makes said scaffolds excellent substrate for cell culture.

It is possible that liquids and (macro-)molecules diffuse into or even pass through the scaffold of the present invention. This permeability, obeying Fick's equation, is a great advantage, if the scaffold is used for tissue engineering. There it is very important that artificial scaffolds allow the exchange of gases, e.g. oxygen, liquids and compounds, e.g. nutrients for and waste of cells. If such exchange is ensured, cells which are in close contact with such scaffolds may proliferate very well.

The mesh of the biocompatible block copolymer is obtained by electro-spinning. The method of electro-spinning is particularly suited to form thin fibers which are deposited on a target making up a mesh structure thereon. Target means a shaped body which can have different forms, e.g. a tubular form. The scaffold according to the present invention comprises fibers of about 5 to 10 μm diameter and an average distance between fibers of approximately 50 μm.

Scaffolds according to the present invention comprise a biocompatible block copolymer. Suitable biocompatible block copolymers have been described in EP 0 696 605 and WO 2005/007210 which are both incorporated herein by reference.

This block copolymer has at least two block units obtainable by linear polycondensation in the presence of diisocyanate, diacid halide or phosgene of a first block unit selected from the group consisting of a diol (I) and an α,ω-dihydroxy-polyester (IV) with a second block unit selected from the group consisting of the same diol (I), a further α,ω-dihydroxy-polyester (II), a α,ω-dihydroxy-polyether (III) and the same α,ω-dihydroxy-polyester (IV).

The diol (I) is obtainable by transesterification of poly-[(R)-(3)-hydroxybutyric acid] or copolymers thereof with 3-hydroxyvaleric acid with ethylene glycol.

The α,ω-dihydroxy-polyester (II) is obtainable by ring-opening polymerization of cyclic esters selected from the group consisting of (L,L)-dilactide, (D,D)-dilactide, (D,L)-dilactide, diglycolide or mixtures thereof, or lactones selected from the group consisting of β-(R)-butyrolactone, β-(S)-butyrolactone, β-rac-butyrolactone and ε-caprolactone or mixtures thereof.

The α,ω-dihydroxy-polyether (III) is selected from the group consisting of α,ω-dihydroxy-poly(oxytetramethylene), α,ω-dihydroxy-poly(oxyethylene) and copolymers of ethylene glycol and propylene glycol.

The α,ω-dihydroxy-polyester (IV) can be obtained by transesterification of α,ω-dihydroxy[oligo(3-(R)-hydroxybutyrate)ethylene-oligo(3-(R)-hydroxybutyrate)] (I), which is referred to hereinafter as PHB diol (IV), with diglycolide dilactide or caprolactone or mixtures thereof, the trans-esterification preferably being carried out in the presence of a catalyst. In the following reaction scheme, m is 1 to 50, n is 1 to 50, x+y is 1 to 50.

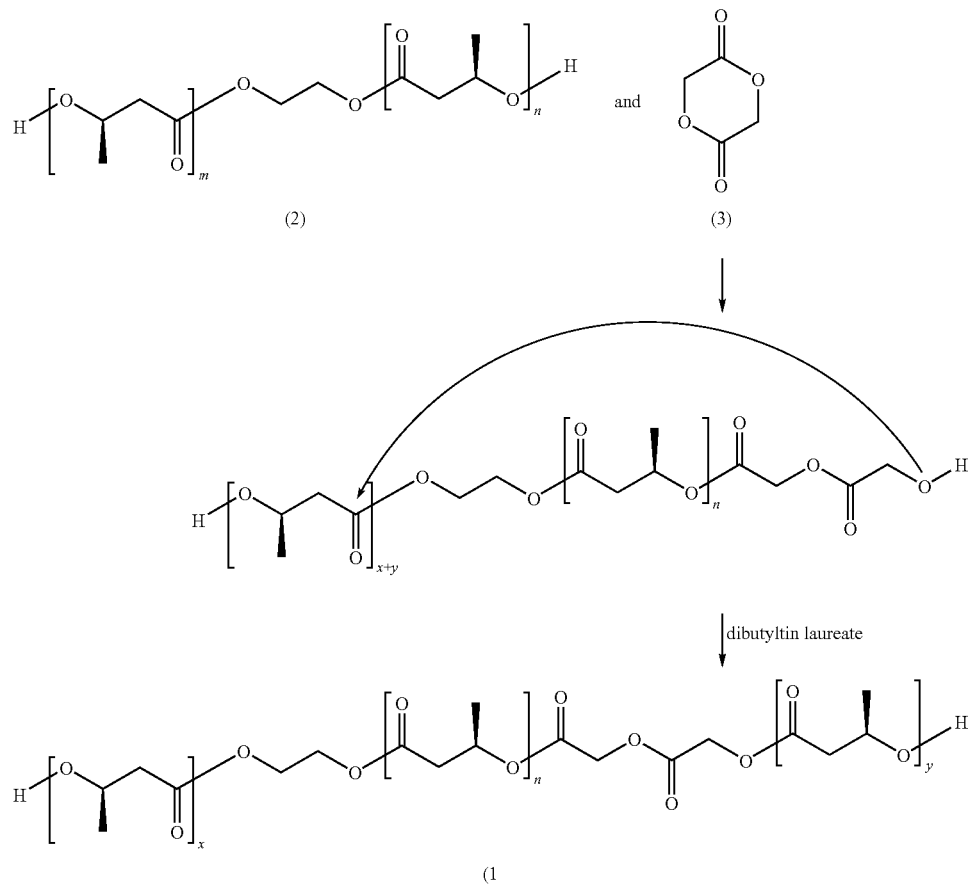

Preferred catalysts are transesterification catalysts in particular based on tin, e.g. dibutyltin dilaurate. The diol preferably has a molecular weight of from 500 to 10'000 daltons. The diol (1) preferably has a total glycolide content of up to 40 mol %, particularly preferably up to 30 mol %. A preferred diol of the invention is α,ω-dihydroxy[oligo(3-R-hydroxybutyrate)-stat-glycolide)ethyleneoligo(3R)-hydroxybutyrate-stat-glycolide) or the corresponding stat-lactide or stat-caprolactate compounds if dilactide or caprolactone is used instead of diglycolide.

Further suitable α,ω-dihydroxypolyesters (II) are oligomers of α-, β-, γ- and ω-hydroxy carboxylic acids and their cooligomers which are obtained by ring-opening polymerization of cyclic esters or lactones. Preferred cyclic esters of this type are (L,L)-dilactide, (D,D)-dilactide, (D,L)-dilactide, diglycolide or the preferred lactones such as β-(R)-butyrolactone, β-(S)-butyrolactone, β-rac-butyrolactone and ε-caprolactone or mixtures thereof. The ring opening takes place with aliphatic diols such as ethylene glycol or longer-chain diols. The molecular weight of the resulting macrodiol is determined by the stoichiometrically employed amount of these diols.

The ring-opening polymerization of the cyclic esters or lactones preferably takes place without diluent in the presence of a catalyst, for example $SnO(Bu)_2$ at 100° C. to 160° C. The resulting macrodiols have molecular weights of about 300-10'000 daltons. The macrodiols prepared from mixtures of cyclic esters or lactones have a microstructure which depends on the amount of catalyst and which is statistical or alternating in the distribution of the monomeric components between block form. The distributions statistics have an influence on the physical properties. Examples of such esters which are obtained by ring-opening polymerization of cyclic esters and lactones in the presence of a catalyst and which can be used to prepare the block copolymers are α,ω-dihydroxy-[poly(L-lactide)-ethylene-poly(L-lactide)]; α,ω-dihydroxy-[oligo(3-(R)-hydroxybutyrate-ran-3-(S)-hydroxybutyrate)-ethylene-oligo(3-(R)-hydroxybutyrate-ran-3-(S)-hydroxybutyrate)]; α,ω-dihydroxy-[oligo(glycolide-ran-ε-caprolactone)-ethylene-oligo(glycolide-ran-ε-caprolactone)]; α,ω-dihydroxy-[oligo(L)-lactide-ran-ε-caprolactone)-ethylene-oligo(L)-lactide-ran-ε-caprolactone)]; α,ω-dihydroxy-[oligo(L)-lactide-ran-glycolide)-ethylene-oligo(L)-lactide-ran-glycolide)]; α,ω-dihydroxy-(oligo(3-(R)-hydroxybutyrate-ran-3-(S)-hydroxybutyrate-ran-glycolide)-ethylene-oligo(3-(R) hydroxybutyrate-ran-3-(S)hydroxybutyrate-ran-glycolide); α,ω-dihydroxy-[oligo-3-(R)-hydroxybutyrate-ran-3-(S)-hydroxybutyrate-ran-L-lactide-ethylene-oligo(3-(R)-hydroxybutyrate-ran-(S)-hydroxybutyrate-ran-L-lactide)] and α,ω-hydroxy-[oligo(3-(R)-hydroxybutyrate-ran-3-(S)-hydroxybutyrate-ran-ε-caprolactone)ethylene-oligo(3-(R)-hydroxybutyrate-ran-3-(3)-hydroxybutyrate-ran-ε-caprolactone)].

The ring-opening polymerization for preparing these macrodiols can also take place without catalyst. Diisocyanates suitable for preparing the polyurethane variant of the block copolymers are in particular hexamethylene diisocyanate, 2,2,4-trimethylhexamethylene diisocyanate, cyclohexyl 1,4-diisocyanate, cyclohexyl 1,2-diisocyanate, isophorone diisocyanate, methylenedicyclohexyl diisocyanate and L-lysine diisocyanate methyl ester.

Diacid halides particularly suitable for preparing the polyester variant of the block copolymers are those of oxalic acid, malonic acid, succinic acid, glutaric acid, adipic acid, pimelic acid, suberic acid, azelaic acid, trimethyladipic acid, sebacic acid, dodecanediacid, tetradecanedioic acid and hexadecanedioic acid.

Reaction to give the polymer of the invention takes place almost quantitatively. It has moreover been found that incorporation of the dilactide, diglycolide and/or caprolactone units results in the polymers of the invention being soluble in methylene chloride. It is thus possible to remove impurities by filtration. A cost-effective process with which the polymer of the invention can be prepared with high purity is provided thereby.

In preferred embodiments the first block unit is the α,ω-dihydroxy-polyester (IV) and the second block unit is either the diol (I), the α,ω-dihydroxy-polyester (II), α,ω-dihydroxy-polyether (III) or the same α,ω-dihydroxy-polyester (IV).

The scaffolds comprising glycolide units which are particularly preferred are those degradable in five to six days within the human or animal body. Further preferred scaffolds are those whose degradation takes place over months or years. The rate of degradation depends primarily on the number of diglycolide or glycolide units. On storage in a neutral buffer solution at 37° C., the molecular weight decreases with time as a function of the glycolide content. The use of dilactide or caprolactone units does not change the rate of degradability of the polymers of the invention in the body.

In a preferred embodiment the scaffolds of the present invention are made of the above described biocompatible block copolymers.

In another preferred embodiment cells, preferably endothelial cells and/or myofibroblasts, are cultured on scaffolds of the present invention. It is possible to culture a single cell type or several different cell types on the scaffold. The structure of the scaffold renders it an excellent substrate for cells. The present open pores provide space for cellular ingrowth and the deposition of extracellular matrix. Since the scaffold provides the necessary mechanical stability and elasticity, cell culture, after a static phase at the beginning, may be done dynamically. This means, cells are for instance cultured in a static environment in cell culture flasks or the like. Subsequently, the cells growing on the scaffold are transferred in perfusion chamber that imitates a dynamic environment. This process influences the further cell growth. For instance, the composition of the extracellular matrix depends on the mechanical strain the cells are exposed to.

Scaffolds of the present invention can be manufactured and used in various forms. In preferred embodiments, the scaffold is either simply tubular or the scaffold has the form of a vessel, preferably a blood vessel.

In further preferred embodiment the scaffold has the form of a heart valve.

In a preferred embodiment the scaffolds have a service time. This service time may be defined as the time which elapses from the time point in which the scaffold comes to the first time into contact with water and the point in time, when the mechanical properties of the material begins to drop down, and the properties of the scaffold become insufficient to fulfill its task, e.g. providing sufficient biomechanical support to the developing tissue. This is, when the scaffold begins to lose mass, is getting brittle or the pore size and shape alters. These changes go in parallel with the changes of the mechanical properties such as tensile strength, elongation to break and modulus of elasticity. The service time of the said scaffolds may be 5 days up to 2 years. Scaffolds having a service time of more than 2 years can also be achieved. Preferably, the service life time of a scaffold according to the present invention is between 14 to 28 days. This range is particularly suited for tissue engineering. On a molecular basis this is the time point, when the macromolecules, building up the biocompatible block copolymer drop below a average molecular weight of about 10'000 Da.

The present invention also relates to valve models that can be used (also termed carrier structures or targets) to manufacture scaffolds according to the present invention. The valve models are subject-matter of claim 12. Further preferred embodiments are subject-matter of the dependent claims.

A valve model for producing a scaffold comprises at least two separate model parts. A first model part has a cylindrical area defining an axis and, adjoining this area, a free end area with at least two end faces. The end faces can be convex and also concave in the axial direction. Plane faces or free faces are also conceivable. In addition, three or more end faces are also possible. Both the cylindrical area, about its circumference, and also the free end area of the first model part are intended to be coated with a polymer.

The second model part has a cylindrical portion defining a further axis, and, adjoining this portion, a free end portion. In a preferred embodiment, the axes of the first model part and of the second model part are aligned with one another. The end faces of the free end portion of the second model part are complementary to the end faces of the free end portion of the first model part. In the second model part, the cylindrical portion is intended to be coated about its circumference with a polymer.

It is also conceivable that, both in the first model part and in the second model part, the cylindrical area and the free end area or, respectively, the cylindrical portion and the free end portion, are intended to be coated with a polymer.

The multi-part construction of the valve model permits demolding of the scaffold as obtained by the electrospinning method, without its being damaged in any way. A concentric threaded bore, which is arranged at the end remote from the free end area (or free end portion) and is present in both model parts, is used to receive magnets as a result of which the two model parts are held together. The threaded bore additionally serves for fastening on a drive shaft of an electrospinning device. In this way, the valve model can be rotated during the spin process.

In a preferred embodiment, the polymer-coated end faces of the free end area of the first model part and the end faces of the free end portion of the second model part can be brought into a position in which they lie opposite one another, a polymer layer being arranged between the end faces in the free end area of the first model part and the end faces in the free end portion of the second model part. The model parts are then present in the assembled state and form the valve model. In this way, it is possible to produce tubular structures, for example, which contain valves or the like in their interior.

The scaffolds produced by means of a valve model according to the invention are in one piece and have no weld seams or like connection points. The scaffold therefore has no weak points, of the kind generally represented by weld seams or the like. The scaffold can be used for tissue cultivation.

In a preferred embodiment, the valve model is a heart valve model. The form of the heart valve model imitates the human heart valve. The heart valve model comprises a first model part and a second model part, which in turn comprise in each case four individual parts.

The scaffold manufactured with the heart valve model needs further processing after its demolding. Since the valve cusps form a single unit, they have to be partly cut out. For this purpose the heart valve scaffold is soaked in cyclohexane and frozen. The frozen heart valve scaffold is taken out of the cyclohexane and the valve cusps are cut apart. Cutting the valve cusps while the scaffold is still frozen provides the necessary stiffness needed for a clean cut.

The first model part comprises a crown part arranged securely on the cylindrical area and three crown attachments. The crown part has radially inwardly offset recesses. The crown attachments have corresponding mating faces and are fitted into the recesses. The crown part and the crown attachments together form, in the free end area, three axially concave end faces, which correspond to the three valve cusps. In the radial direction to the axis, the crown part and the crown attachments of the first model part form three convex side faces which adjoin the cylindrical area and the end faces of the free end area. The convex side faces are intended to be coated with a polymer.

The second model part comprises a mating crown part arranged securely on the cylindrical portion and three mating crown attachments. The mating crown part has radially inwardly offset recesses into which the mating crown attachments fit with their corresponding mating faces. The three mating crown attachments form, in the free end portion of the second model part, three axially convex end faces which are complementary to the end faces of the free end area of the first model part. In addition, the crown attachments form, in the radial direction, three convex side faces which adjoin the cylindrical portion and the end faces of the free end portion of the second model part. The convex side faces correspond to valve pockets. The convex side faces are intended to be coated with a polymer.

The valve cusps are preferably arranged at an angle of at least approximately 120° relative to one another. This applies also to the valve pockets. Moreover, the arrangement of the valve cusps and of the valve pockets is configured such that each valve cusp can be pressed in the direction of flow into a valve pocket.

In another preferred embodiment, the end faces of the free end area of the first model part are concave in the axial direction. This corresponds to the natural form of valve cusps and is advantageous for their function.

In a preferred embodiment, the valve model is a vein valve model. In this case, the first model part has a free end area with only two end faces. The end faces in the free end portion of the second model part are intended to lie opposite the end faces in the free end area of the first model part and are accordingly of a complementary design.

In a preferred embodiment, the valve model comprises an electrically conductive material. This material is preferably a metal or a metal alloy. The valve model can be made of metal or of a metal alloy or can comprise further materials, for example the valve model can be coated with a polymer such as Teflon or another synthetic. Valve models according to the invention can thus be coated with polymers by the electrospinning method. The electrospinning method is familiar to a person skilled in the art.

BRIEF DESCRIPTION OF THE SEVERAL VIEWS OF THE DRAWINGS

The valve model according to the invention is explained in more detail below with reference to the illustrative embodiments depicted purely schematically in the drawings, in which.

DETAILED DESCRIPTION OF THE INVENTION

Figure 1:
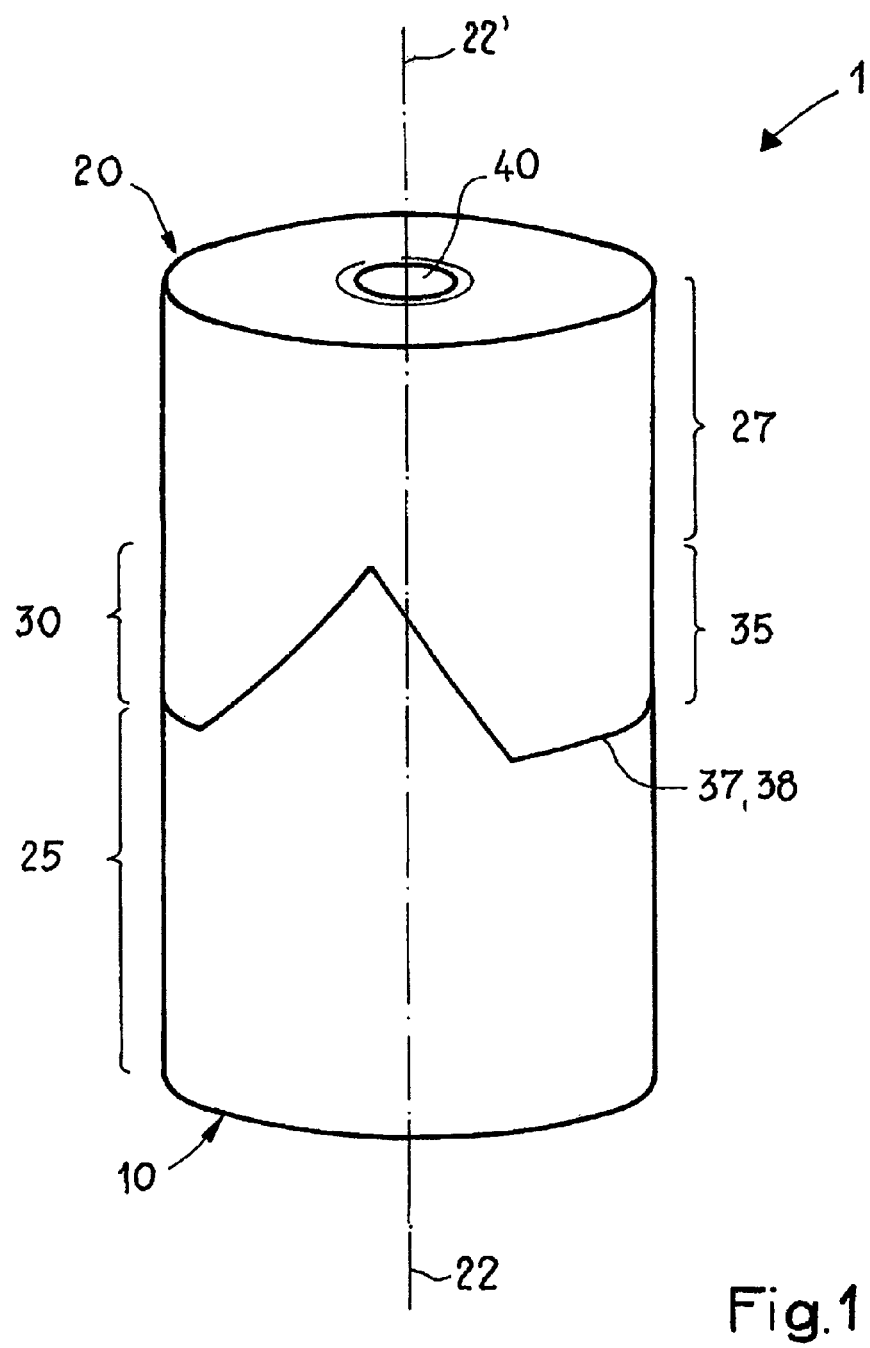
FIG. 1 shows a perspective view of an assembled two-part valve model according to the present invention.

FIG. 1 shows a two-part valve model 1 according to the invention in the assembled state. The valve model 1 is made up of a first model part 10 and of a second model part 20. The first model part and second model part in each case define an axis 22 and 22', respectively. The first model part 10 has a circular cylindrical area 25 and, adjoining this, a free end area 30. The second model part 20 has a likewise circular cylindrical portion 27 and, adjoining this, a free end portion 35. The axis 22 of the first model part 10 is aligned with the further axis 22' of the second model part 20 in the assembled state. The free end area 30 of the first model part 10 lies opposite the free end portion 35 of the second model part 20 in the assembled state shown here. Partially visible in the figure are the delimiting edges 37 and 38 of the end faces 50 and 60, not visible in the assembled state, of the first model part 10 and of the second model part 20.

The circular cylindrical area 25, about its circumference, and the free end area 30 of the first model part 10 are intended to be coated with a polymer. In the second model part 20, the circular cylindrical portion 27 is intended to be coated with a polymer.

Visible in the second model part 20 is a concentrically arranged threaded bore 40 arranged at the end of the model part remote from the free end portion 35. Both model parts 10 and 20 have this threaded bore 40. It serves on the one hand to hold a magnet, as a result of which the first model part 10 and the second model part 20 are held together, and, on the other hand, the first model part 10 or the second model part 20 can be fastened via this threaded bore 40 on a drive shaft of an electrospinning device.

The individual parts of the valve model 1 are positioned by dowel pins and are held by screws. Other types of connection are also conceivable.

Figure 2:
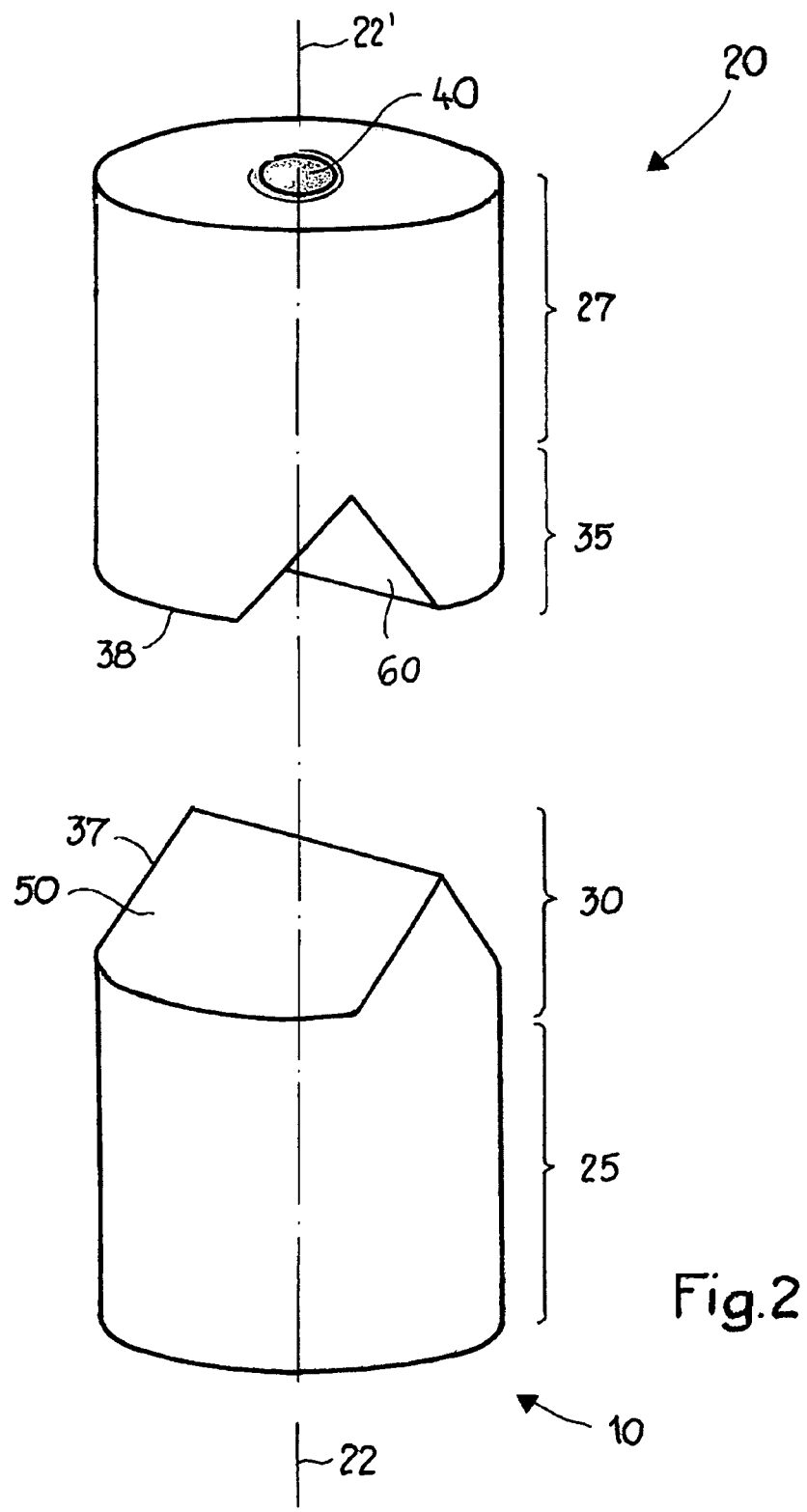
FIG. 2 shows, in the same format as FIG. 1, a first model part and a second model part of the valve model from FIG. 1, in a position spaced apart from one another.

FIG. 2 shows the first model part 10 and the second model part 20 from FIG. 1 in a position axially spaced apart from one another. Again the threaded bore 40 is visible only on the second model part 20. The first model part 10 has two end faces 50 in the free end area 30. In the present embodiment, the end faces 50 are plane and arranged in a gable roof shape.

However, other embodiments are also possible in which the end faces 50 in the free end area 30 of the first model part 10 have axially concave end faces, convex end faces or free faces. In the free end portion 35, the second model part 20 has two end faces 60. The end faces 60 are complementary to the end faces 50 of the first model part 10 and intended, in the assembled state, to lie opposite the end faces 50 of the first model part 10.

In the first model part 10, the circular cylindrical area 25, about its circumference, and the free end area 30 are intended to be coated with polymer. In the second model part 20, the circular cylindrical portion 27 is intended to be coated, about its circumference, with polymer.

In a first step in the production of a scaffold according to the invention the circular cylindrical area 25, about its circumference, and the free end area 30 of the first model part 10 are coated with a polymer by means of the electrospinning method. The first model part 10 and the second model part 20 are then joined together in the axial direction, a polymer layer being located between the end faces 50 and 60 of the two model parts 10 and 20. The circular cylindrical portion 27 of the second model part 20 is then coated with polymer by means of the electrospinning method, the polymer coating extending beyond the delimiting edges 38. The one-piece scaffold according to the invention is formed in this way.

Figure 3:
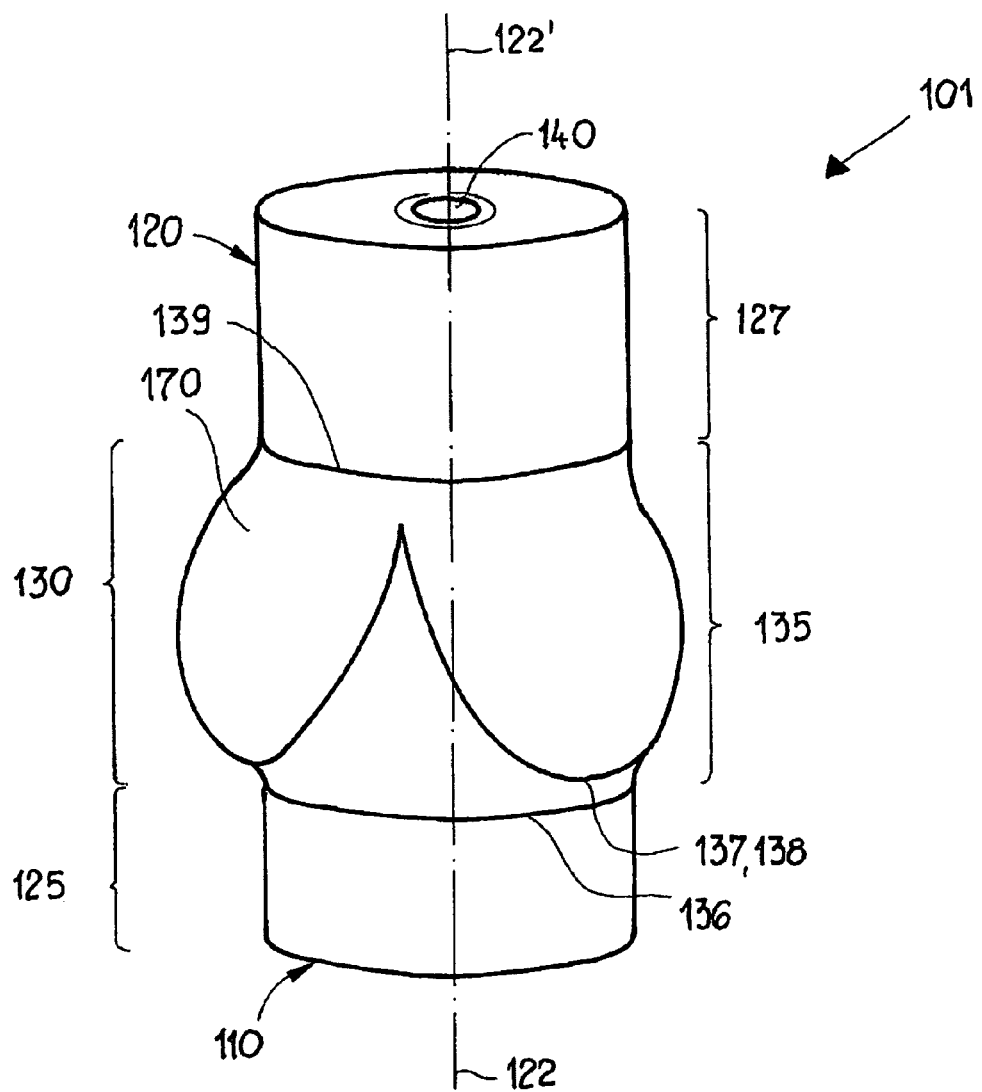
FIG. 3 shows a perspective view of a heart valve model according to the invention in the assembled state.

FIG. 3 shows a heart valve model 101 in the assembled state. The heart valve model 101 comprises a first model part 110 and a second model part 120. The first model part 110 and the second model part 120 in each case define an axis 122 and 122', respectively. The first model part 110 again has a circular cylindrical area 125 and a free end area 130. The second model part 120 has a circular cylindrical portion 127 and a free end portion 135. The free end area 130 and the free end portion 135 of the first model part 110 and of the second model part 120, respectively, lie opposite one another in the assembled state, with the axes 122 and 122' lying aligned.

The delimiting edges 136 and 139 of the circular cylindrical areas 125 and 127 of the first model part 110 and second model part 120, respectively, are only partially visible. Also only partially visible are the delimiting edges 137 and 138 of the end faces 150 and 160 (not seen in this figure) of the two model parts 110 and 120.

A threaded bore 140 is visible only in the second model part 120, although this threaded bore 140 is also present in the first model part 110. The threaded bores 140 are concentric at the end lying remote from the free end area 130 of the first model part 110 and from the free end portion 135 of the second model part 120, and they are intended to receive magnets, in particular permanent magnets, by means of which the first model part 110 and the second model part 120 are held together. In addition to this, the threaded bore 140 serves for fastening the first model part 110 or the second model part 120 on a drive shaft of an electrospinning device.

The side faces 170 in the free end portion 135 of the second model part 120 correspond to the valve pockets of a heart valve.

Figure 4:
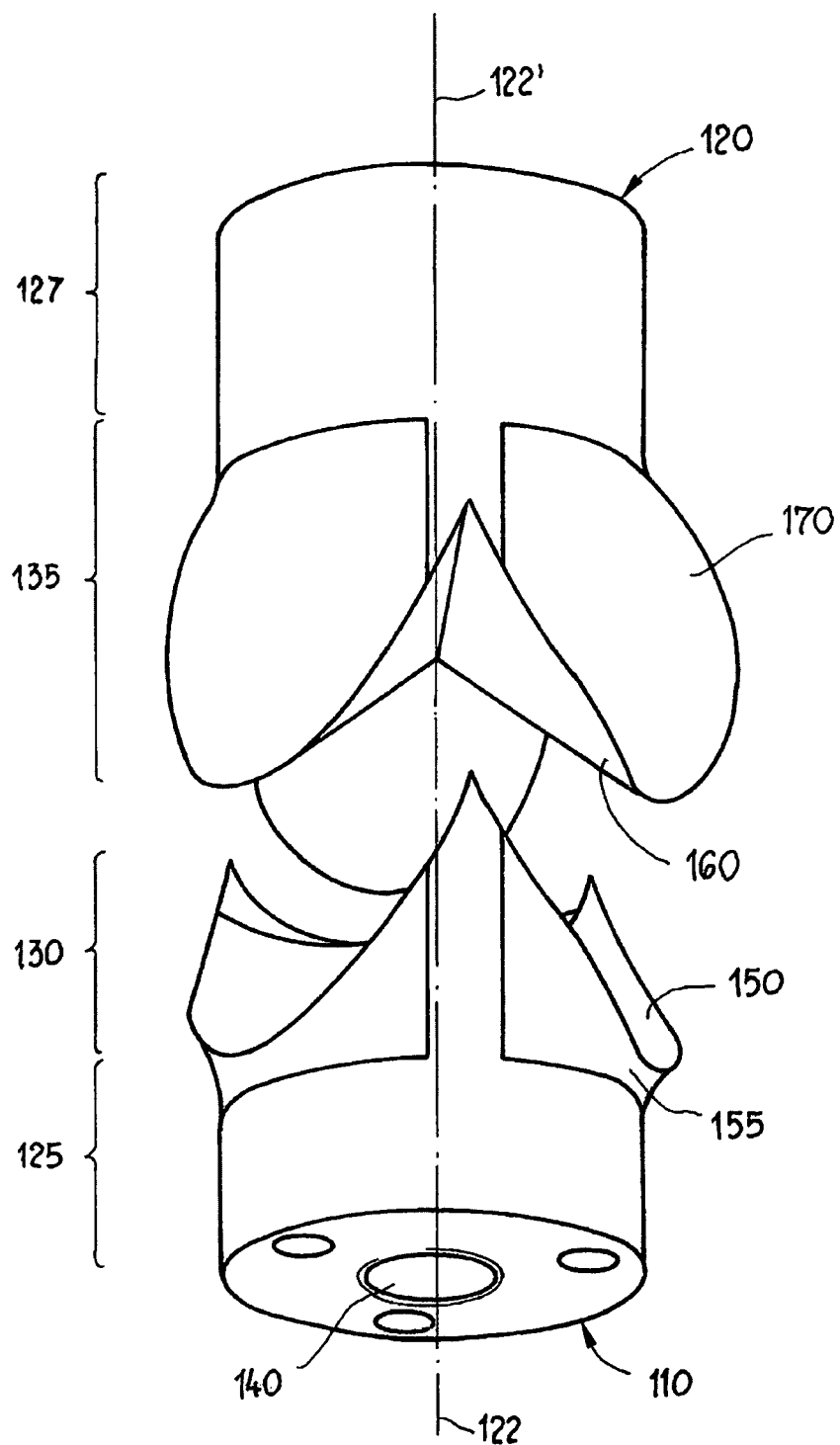
FIG. 4 shows a perspective view of a first model part and second model part of the heart valve model from FIG. 3, in a position spaced apart from one another.

In FIG. 4, the first model part 110 and the second model part 120 of the heart valve model 101 from FIG. 3 are shown at an axial distance from one another. In contrast to FIG. 3, here the threaded bore 140 is visible in the first model part 110. The threaded bore is concentrically arranged at the end of the first model part 110 remote from the free end area 130. The threaded bore 140 serves in turn for receiving magnets and for fastening to a drive shaft of an electrospinning device.

The figure also shows the circular cylindrical area 125 and the adjoining free end area 130 of the first model part 110 and the circular cylindrical portion 127 and adjoining free end portion 135 of the second model part 120. In the free end area 130 of the first model part 110, it has three contiguous end faces 150 that are concave in the axial direction, the axis 122 being defined by the cylindrical area. The end faces 150 of the first model part 110, which are concave in the axial direction, correspond in terms of their form to valve cusps. In the radial direction, the first model part 110 has three convex side faces 155 which adjoin the cylindrical area 125 and the end faces 150. The cylindrical area 125 and the free end area 130 of the first model part 110 are intended to be coated with a polymer.

The second model part 120 also defines an axis 122' through the circular cylindrical portion 127 and has, in the adjoining free end portion 135, three contiguous end faces 160 which are complementary to the three end faces 150 of the first model part 110 and lie opposite these in the assembled state. Since the three end faces 160 in the free end portion 135 of the second model part 120 are complementary to the three end faces 150 in the free end area 130 of the first model part 110, the three end faces 160 in the free end portion 135 of the second model part 120 have a convex form in the axial direction. The second model part 120 additionally has, in the free end portion 135, three side faces 170 which are convex in the radial direction to the axis 122' and which adjoin the cylindrical portion 127 and the end faces 160 of the second model part 120 and correspond to valve pockets. The circular cylindrical portion 127 and the side face 170 of the second model part 120 are intended to be coated with a polymer.

Figure 5:
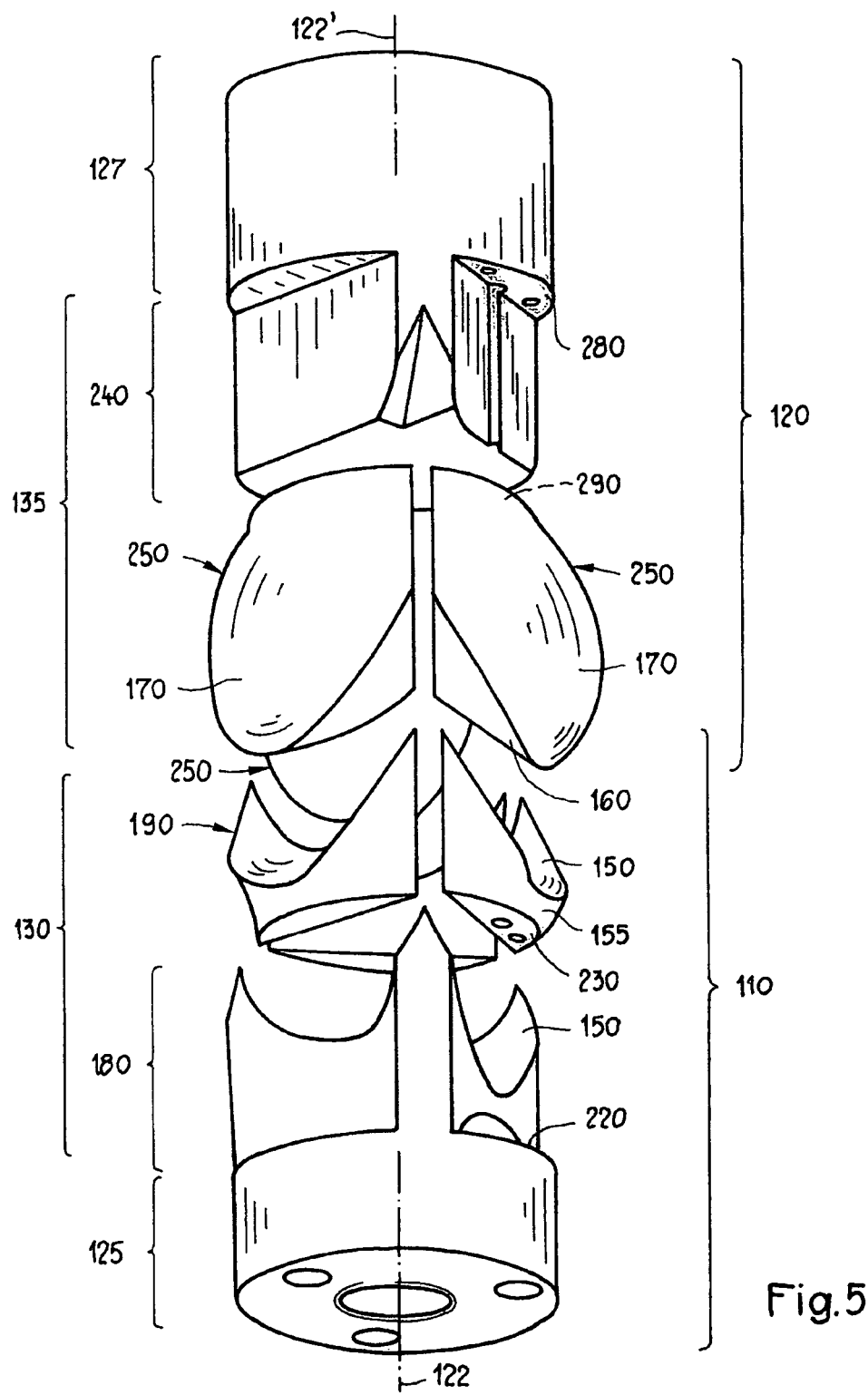
FIG. 5 shows an exploded view of the model part 1 from FIG. 4 broken up into its individual parts, and of the model part 2 from FIG. 4 broken up into its individual parts.

FIG. 5 shows the first model part 110 and the second model part 120 from FIG. 4, which are each shown there in an assembled state. The individual components of the two model parts 110 and 120 are now shown here. The first model part 110 has four parts, namely a crown part 180 arranged securely on the cylindrical area 125, and three crown attachments 190. The crown part 180 has, radially with respect to the axis 122, recesses 220 that are inwardly offset in relation to the circumferential surface of the circular cylindrical area. The crown attachments 190 have corresponding mating faces 230 and are fitted into the recesses. The crown part 180 and the crown attachments 190 together form in the free end area 130, in the axial direction, the three concave end faces 150 which correspond to the three valve cusps of a heart valve, and in the radial direction they form the three convex side faces 155.

The second model part 120 has a mating crown part 240 arranged securely on the cylindrical portion, and three mating crown attachments 250. The mating crown part 240 has, radially with respect to the axis 122', recesses 280 that are inwardly offset in relation to the circumferential surface of the circular cylindrical portion 127. The mating crown attachments 250 have corresponding mating faces 290 and are fitted into the recesses. The mating crown attachments 250 form, in the free end portion 135 of the second model part 120 three end faces 160 which are convex in the axial direction and are complementary to the end faces 150 of the free end area 130 of the first model part 110. In the radial direction to the axis 122', the mating crown attachments 250 form three convex side faces 170 which adjoin the cylindrical portion 127 and the end faces 160. The side faces 170 correspond to the valve pockets of a heart valve.

The axially concave end faces 150 in the free end area 130 of the first model part 110 are arranged at least approximately at an angle of 120° relative to one another. This applies also to the axially convex end faces 160 in the free end portion 135 of the second model part 120. The radially convex side faces 170 in the free end portion 135 of the second model part 120 which correspond to the three valve pockets of a heart valve are likewise arranged at an angle of at least approximately 120° relative to one another and also in such a way that the valve cusps can be moved into the valve pockets in the direction of flow, from the bottom upward in FIG. 5.

The coating with polymer is effected is a similar way to that described with reference to FIGS. 1 and 2. In the first model part 110, the circular cylindrical area 125, about its circumference, and the free end area 130 are intended to be coated with polymer, and, in the second model part 120, the circular cylindrical portion 127 is intended to be coated, about its circumference, with polymer.

Figure 6:
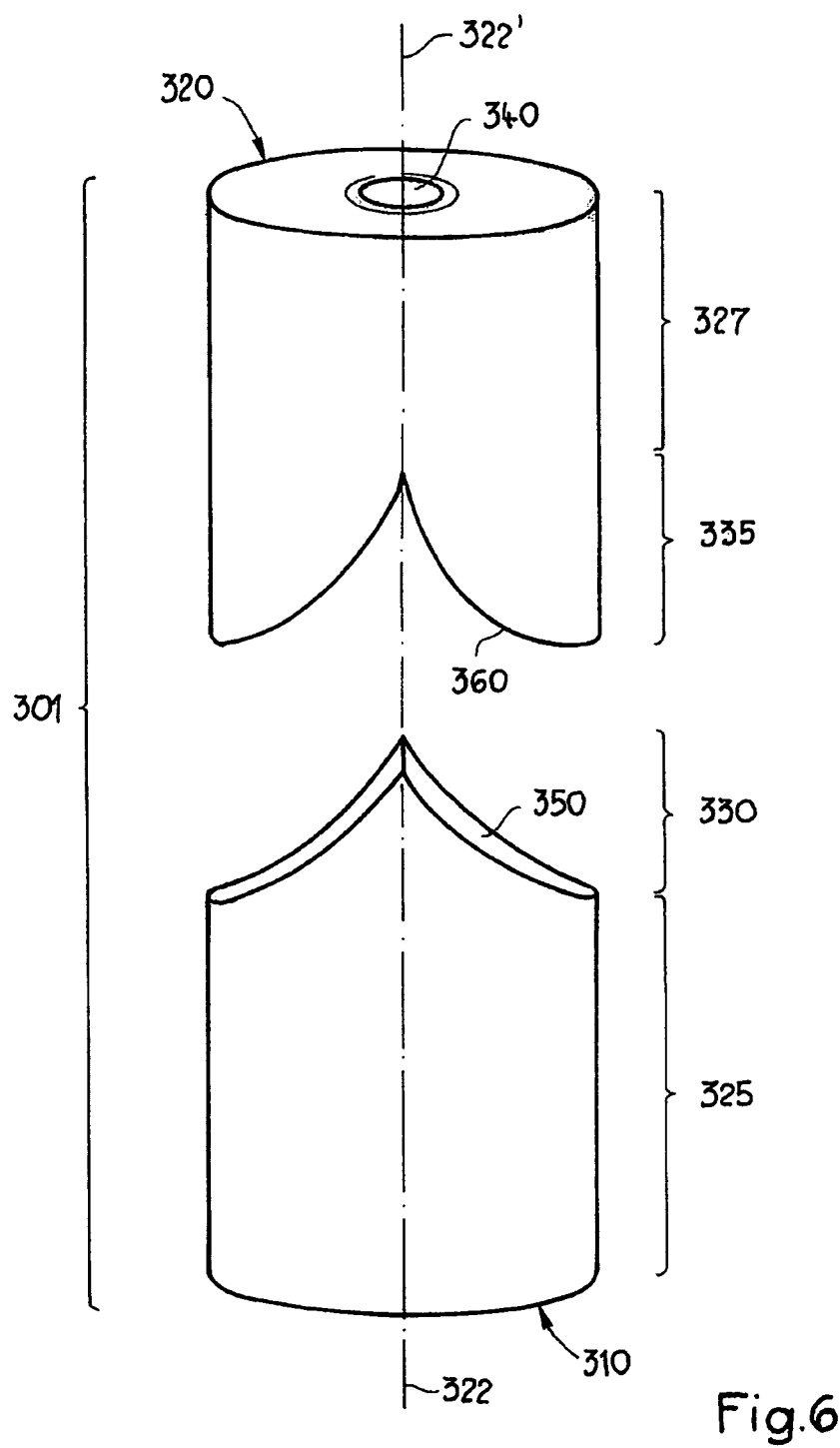
FIG. 6 shows model a perspective view of a vein valve according to the invention, with first part and second model part shown spaced from one another.

FIG. 6 shows a vein valve model 301. The vein valve model 301 comprises a first model part 310 and a second model part 320. The first model part 310 has a cylindrical area 325 and a free end area 330. The second model part 320 has a cylindrical portion 327 and a free end portion 335. Both the first model part 310 and the second model part 320 define, through their respective, cylindrical areas 325 and 327, axes 322 and 322', respectively, which are aligned in the assembled state of the two model parts 310 and 320.

At the end remote from the free end portion 335, the second cylindrical model part 320 has a threaded bore 340 which is arranged concentric to the axis 322'. The threaded bore 340 is intended to receive magnets and also serves for fastening the model part on a drive shaft of an electrospinning device. The threaded bore 340 of the first cylindrical model part 310 is not visible in this figure.

In the free end area 330, the first cylindrical model part 310 has two end faces 350 which are again shaped like a gable roof in the embodiment shown but are formed concavely in the axial direction. Surfaces that are convex in the axial direction, plane faces and free faces are also conceivable. The cylindrical area 325 and the free end area 330 of the first model part 310 are intended to be coated with a polymer.

In the free end portion 335, the second model part 320 has two end faces 360 which are complementary to the end faces 350 in the free end area 330 of the first model part 310, that is to say are convex in the axial direction. The end faces 360 in the free end portion 335 of the second model part 320 can be brought into a position lying opposite the end faces 350 of the free end area 330 of the first model part 310.

In the second cylindrical model part 320, the cylindrical portion 327 is intended to be coated with a polymer.

It is conceivable that the above-described circular cylindrical areas or portions also have other cross sections, for example oval. Moreover, it is also possible that the axes of the two model part are not aligned in the assembled state, but instead form an angle.

The present invention also relates to a method according to claim 18 for producing scaffolds of the present invention. Further preferred embodiments are subject-matter of the dependent claims.

The method comprises the steps
a) manufacturing a suitably formed carrier structure;
b) disposing a biocompatible polymer mesh on said carrier structure by electro-spinning
c) removing the carrier structure from the scaffold.

The carrier structure (also termed target) defines the form the scaffold will have. For instance, the carrier structure has a tubular form which does not comprise structural elements within the tubular form. However, the carrier structure may also have more complicated form, e.g. that of a vessel, preferably a blood vessel, or a heart valve. Such carrier structures allow the production of complicated tubular or tubular-like structures including structural elements that are located within the tubular or tubular-like carrier structure.

The polymer, preferably one of the above described polymers, is deposited on the carrier structure by electro-spinning. The electro-spinning process is known the a skilled person. To a certain extent the spinning process may be used to influence the structural properties of the polymer mesh. That means a tubular structure which must be rotated in order to deposit polymer on the entire surface of the carrier structure can be rotated at different speeds. Rotation at lower speeds yields a mesh comprising more irregularly deposited fibers whereas rotation at higher speeds yields a mesh comprising fibers a more regular deposition.

After deposition of the polymer on the carrier structure the latter has to be removed (demolding). Such removal is possible since carrier structure of the present invention comprise at least two separate parts that can be remove step by step.

The present invention also relates to the use of scaffolds of the present invention for tissue engineering or as implants.

Example

Manufacturing of a Tubular Structure

Tubular structures according to the invention can be manufactured using a conventional electro-spinning device. Briefly, a high voltage (e.g. 20 kV) is applied to a metallic capillary, which is connected to a reservoir holding a solution of the biocompatible block copolymer (e.g. 30% in chloroform). The charged polymer solution ejects as a thin jet from the capillary nozzle.

The resulting fibres are then collected on a oppositely charged carrier structure (also termed target). If tubular structures are to be manufactured, a simple electro-conductive bar can be used as target. During the deposition process of the fibres the target is rotated. The rotation speed allows to a certain extent to influence the orientation of the fibres deposited on the target. While low rotation speeds yield a mesh with fibres having no particular orientation, higher rotations speeds yield a mesh with fibres that are oriented.

The invention claimed is:

1. Scaffold comprising an electro-spun mesh of a biocompatible block-copolymer, wherein said scaffold has about 90% open pores and a mesh-like structure formed by polymer fibers of about 5 to 10 μm diameter, and wherein said block copolymer has at least two block units obtainable by linear polycondensation in the presence of diisocyanate, diacid halide or phosgene
    of first block unit selected from the group consisting of a diol (I) and an α,ω-dihydroxy-polyester (IV) with a second block unit selected from the group consisting of the same diol (I), an α,ω-dihydroxy-polyester (II), an α,ω-dihydroxy-polyether (III), and the same α,ω-dihydroxy-polyester (IV),
    wherein the diol (I) is obtainable by transesterification of poly-[(R)-(3)-hydroxybutyric acid] or copolymers thereof with 3-hydroxyvaleric acid with ethylene glycol,
    wherein the α,ω-dihydroxy-polyester (II) is obtainable by ring-opening polymerization of cyclic esters selected from the group consisting of (L,L)-dilactide, (D,D)-dilactide, (D,L)-dilactide, diglycolide or mixtures thereof, or lactones selected from the group consisting of β-(R)-butyrolactone, β-(S)-butyrolactone, β-rac-butyrolactone and ε-caprolactone or mixtures thereof,
    wherein the α,ω-dihydroxy-polyether (III) is selected from the group consisting of α,ω-dihydroxy-poly(oxytetramethylene), α,ω-dihydroxy-poly(oxyethylene) and copolymers of ethylene glycol and propylene glycol,
    wherein the α,ω-dihydroxy-polyester (IV) is obtainable by trans-esterification of the diol (I) with diglycolide and/or dilactide and/or caprolactone or mixtures thereof.

2. Scaffold according to claim 1, wherein the first block unit is the α,ω-dihydroxy-polyester (IV) and the second block unit is the diol (I).

3. Scaffold according to claim 1, wherein the first block unit is the α,ω-dihydroxy-polyester (IV) and the second block unit is the α,ω-dihydroxy-polyester (II).

4. Scaffold according to claim 1, wherein the first block unit is the α,ω-dihydroxy-polyester (IV) and the second block unit is the α,ω-dihydroxy-polyether (III).

5. Scaffold according to claim 1, wherein the first block unit is the α,ω-dihydroxy-polyester (IV) and the second block unit is the same α,ω-dihydroxy-polyester (IV).

6. Scaffold according to claim 1, wherein the scaffold is made of said block copolymer.

7. Scaffold according to claim 1, wherein cells are cultured on said scaffold.

8. Scaffold according to claim 1, wherein the scaffold has a tubular form.

9. Scaffold according to claim 1, wherein the scaffold has a form of a vessel.

10. Scaffold according to claim 1, wherein the scaffold has a form of a heart valve.

11. Scaffold according to claim 1, wherein the scaffold is hydrolytically degradable and has a controllable service life time and keeps its performance from 5 days up to 2 years.

12. Scaffold according to claim 7, wherein said cells are selected from the group consisting of endothelial cells and myofibroblasts.

13. Scaffold according to claim 9, wherein said scaffold has a form of a blood vessel.

14. Method for producing the scaffold for tissue engineering according to claim 1, comprising the steps
    a) manufacturing a suitably formed carrier structure;
    b) disposing the biocompatible block-copolymer as the mesh-like structure on said carrier structure by electrospinning; and
    c) removing the carrier structure from the scaffold.

15. Method according to claim 14, wherein the carrier structure is cooled by cooling means.

16. Method according to claim 15, wherein the cooling means are cold gases, preferably nitrogen or $CO_2$.

17. Method according to claim 14, wherein the carrier structure has a tubular form.

18. Method according to claim 14, wherein the carrier structure has a form of a vessel.

19. Method according to claim 14, wherein the carrier structure has a form of a heart valve.

* * * * *

UNITED STATES PATENT AND TRADEMARK OFFICE
CERTIFICATE OF CORRECTION

PATENT NO.         : 8,562,671 B2
APPLICATION NO.    : 12/303897
DATED              : October 22, 2013
INVENTOR(S)        : Peter Neuenschwander It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 310 days.

Signed and Sealed this

Fifteenth Day of September, 2015

Michelle K. Lee
*Director of the United States Patent and Trademark Office*